United States Patent [19]

Burton et al.

[11] 4,392,562
[45] Jul. 12, 1983

[54] LIMITED BEND MALLEABLE PENILE PROSTHESIS

[75] Inventors: John H. Burton, Minnetonka; Michael A. Mikulich, St. Paul, both of Minn.

[73] Assignee: American Medical Systems, Inc., St. Louis Park, Minn.

[21] Appl. No.: 275,288

[22] Filed: Jun. 19, 1981

[51] Int. Cl.³ .............................................. A61F 5/00
[52] U.S. Cl. ............................................. 128/79; 3/1
[58] Field of Search .................................. 128/79; 3/1

[56] References Cited

U.S. PATENT DOCUMENTS

| 3,893,456 | 7/1975 | Small et al. | 128/79 |
| 3,987,789 | 10/1976 | Timm et al. | 128/79 |
| 4,066,073 | 1/1978 | Finney et al. | 128/79 |
| 4,151,840 | 5/1979 | Barrington | 128/79 |
| 4,177,805 | 12/1979 | Tudorin | 128/79 |

Primary Examiner—Stephen C. Pellegrino
Attorney, Agent, or Firm—Williamson, Bains, Moore & Hansen

[57] ABSTRACT

A prosthesis adapted to be implanted in a penis includes an elongate malleable element which may be bent to enable the prosthesis to be conformed to a variety of shapes. A bend-limiting member is positioned next to the malleable element and serves to limit the radius of bend of the malleable element and thereby minimize damage or weakening to the malleable element through extreme bending. The malleable element and the bend-limiting member are encased within a physiologically inert plastic body.

11 Claims, 9 Drawing Figures

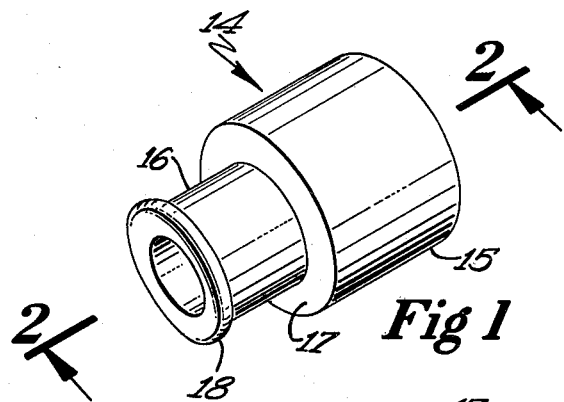
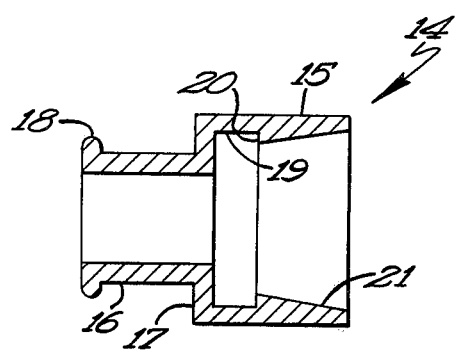
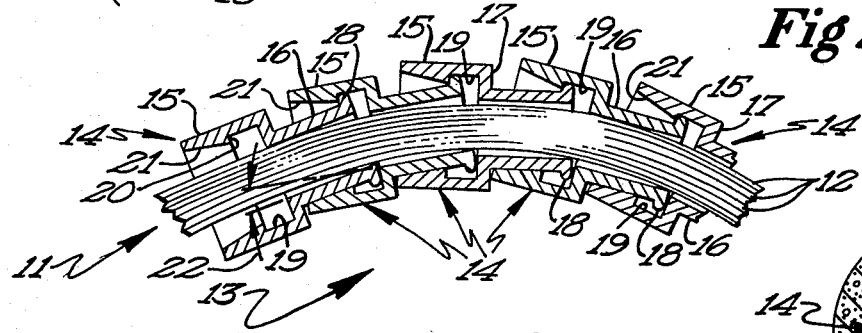
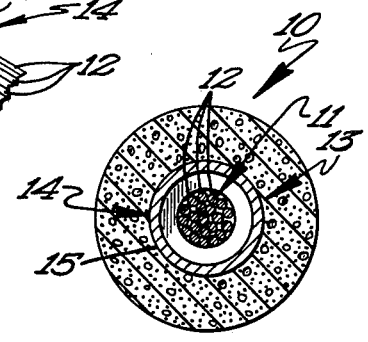
Fig 1
Fig 2
Fig 3
Fig 8
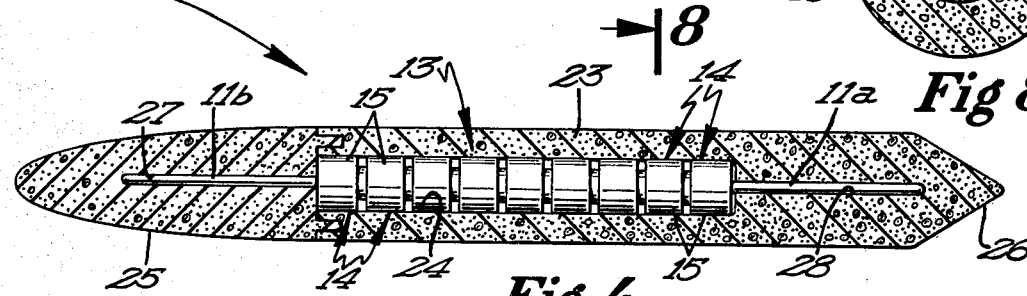
Fig 4
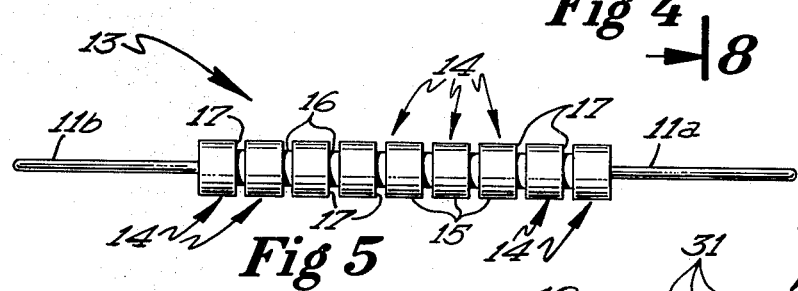
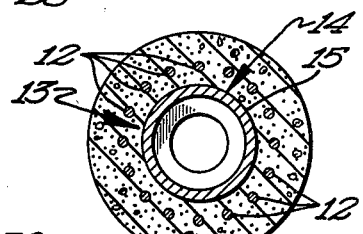
Fig 5
Fig 9
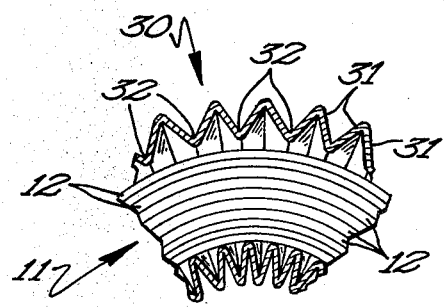
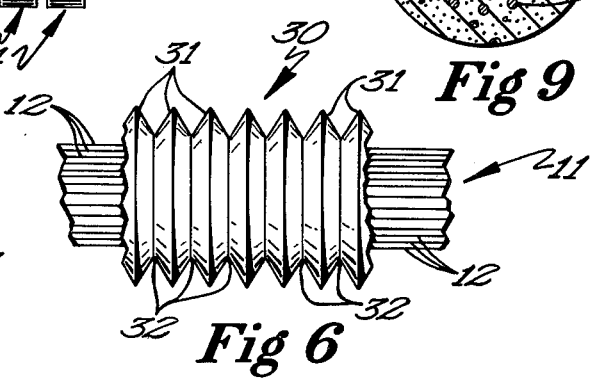
Fig 7
Fig 6

LIMITED BEND MALLEABLE PENILE PROSTHESIS

BACKGROUND OF THE INVENTION

This invention relates to a penile prosthesis, and, more particularly, to an improved malleable penile prosthesis for the treatment of erectile impotence.

There are many causes of male impotence including those that are psychologically based as well as trauma related impotence. Procedures have been developed for treating impotence, and one such procedure involves the implantation of a penile prosthesis. There are two general types of penile implants, namely, the inflatable penile implant and the noninflatable penile implant. The noninflatable implants include those which incorporate a rigid rod and are permanently stiff and those formed of malleable or bendable materials and which may be bent between the erect and nonerect positions. U.S. Pat. No. 3,893,456 discloses a rigid rod type of penile prosthesis. Examples of malleable implants are shown in U.S. Pat. No. 3,987,789 and U.S. Pat. No. 4,151,841. One of the problems involved in malleable penile implants which are bent between the erect and nonerect positions is the danger of stress or weakening of the malleable element when bent beyond a predetermined radius. It will be appreciated that when the malleable element is bent so that its radius of bend is quite small, then stress or weakness is developed at a concentrated zone. Repeated bending will occur at the weakened point which ultimately may result in failure. Also, concentration of the bend in a short length may result in an uncosmetic, kinked appearance.

Certain noninflatable prostheses have been developed which permit bending in one direction only, such as disclosed in U.S. Pat. No. 4,177,805 and the German patent to Max Bernhard Ulrich, filed Sept. 7, 1977, German Pat. No. 27 40 263. However, there are no prior art devices which limit the bending in all directions but which permit ready manipulation of the implant between the erect and the nonerect positions.

SUMMARY OF THE INVENTION

An object of this invention is to provide a novel malleable penile implant, of simple and inexpensive construction, which may be readily manipulated by bending between erect and non-erect positions without the attendant danger of stressing and weakening the prosthesis by extreme bending.

A more specific object of this invention is to provide an improved mallable penile implant which is provided with bend-limiting means to limit the radius of bending of the prosthesis when the latter is manipulated between the erect and non-erect position to thereby minimize, if not preclude, damage to the prosthesis by extreme bending.

These and other objects and advantages of this invention will more fully appear from the following description made in connection with the accompanying drawings, wherein like reference characters refer to the same or similar parts throughout the several views.

FIGURES OF THE DRAWINGS

FIG. 1 is a perspective view of one of the elements comprising the bend-limiting member of the prosthesis;

FIG. 2 is a cross-sectional view taken approximately along line 2—2 of FIG. 1 and looking in the direction of the arrows;

FIG. 3 is a cross-sectional view of the bend-limiting member with the malleable element being disposed interiorly thereof;

FIG. 4 is a cross-sectional veiw of the prosthesis;

FIG. 5 is a side elevational view of the bend-limiting member and malleable element illustrated in an erect condition;

FIG. 6 is a fragmentary, side elevation view of a different embodiment of the bend-limiting member positioned around the malleable element, and illustrated in an erect condition;

FIG. 7 is a cross-sectional view of the embodiment illustrated in FIG. 6 but illustrated in a flexed or bent condition.

FIG. 8 is a cross-sectional view of the embodiment of FIG. 4 taken along lines 8—8 thereof; and FIG. 9 is a section view similar to FIG. 8 but showing a different embodiment of the prosthesis.

DESCRIPTION OF THE PREFERRED EMBODIMENT

Referring now to the drawings and, more particularly, to FIG. 4, it will be seen that one embodiment of the penile prosthesis, designated generally by the reference numeral 10, is thereshown. The prosthesis 10 includes an elongate malleable element, designated generally by the reference numeral 11 and illustrated in FIG. 3 and which is comprised of a plurality of strands or filaments 12.

It is preferred that the strands 12 be disposed in parallel relation, although the strands may also be twisted, and it is also preferred that the strands be formed of a malleable substance such as stainless steel or other biocompatible metals. It will be appreciated that other malleable metals such as alloys of silver, gold, or cobalt may be used to form the strands 12. Although the preferred embodiment of the malleable element 11 is illustrated as being comprised of strands or filaments, it is also pointed out that the malleable element can also be formed of generally solid construction as disclosed in U.S. Pat. No. 3,987,789, entitled "Malleable Penile Prosthesis."

The prosthesis 10 also includes an elongate, somewhat flexible, bend-limiting member 13 which is comprised of a plurality of substantially identical tubular elements 14. It is preferred that the tubular elements 14 be formed of a relatively hard, noncorrosive metal, such as tempered stainless steel. Each tubular element 14 includes a large end portion 15 and a small end portion 16, each being of cylindrical configuration and being connected by shoulder 17 defined therebetween. The outer or free end of the small end portion of each tubular element is provided with an outturned bead 18, as best seen in FIGS. 1 and 2.

Referring again to FIGS. 2 and 3, it will be seen that each tubular element 14 is also provided with an annular recess 19 interiorly of the large end portion 15 thereof adjacent the shoulder 17. The annular recess 19 defines an internal shoulder 20 and it will be noted that the interior surface of the large end portion 15 of each tubular element tapers inwardly in an axial direction towards the shoulder 20. With this arrangement it will be seen that the small end portion 16 of each tubular element is inserted into the large end portion 15 of the next adjacent tubular element so that the bead 18 snaps into the annular recess 19 and is prevented from disengagement therefrom by the shoulder 20. It will be appreciated that the external diameter of the small end portion 16 is less than the internal diameter of the smallest diameter of the frustro conical interior of the large end portion 15 of each tubular element. Therefore each adjacent tubular element may be moved angularly with respect to the adjacent tubular element because of this loose fit.

It will therefore be seen that the bend-limiting member 13 deflects over its entire length about a radius defined by the angular deflection between each adjacent tubular element 14, as best seen in FIG. 3. This angular deflection is defined by the angle 22, as designated in FIG. 3. Expressed mathematically, the radius of bend is $r = (L/\sin\theta)$ where L is the axial dimension of the small end portion 16 of the tubular element and $\theta$ is the angle 22. It will therefore be seen that the malleable element can be bent to the nonerect or out of the way position but is limited in its bending to a predetermined radius by the bend-limiting member. The radius of bending of the bend-limiting member, while being sufficient to permit bending of the prosthesis 10 between the erect and nonerect position, prevents acute bending of the malleable element and therefore precludes the concentration of bend stresses at any point along the length dimension of the malleable element. Thus, the bend-limiting member serves to assure uniform bending of the prosthesis when manipulated between the erect and nonerect positions.

The prosthesis is enclosed in a physiologically inert, elastic envelope 23 which is soft and which is provided with an axial recess 24 for receiving the malleable element and bend-limiting member therein. The envelope 23 is preferably made of very soft silicone or silicone gel within an outer silicone sleeve. This lessens the risk of tissue erosion due to pressure points between tissue and the prosthetic device. The silicone envelope 23 includes a proximal end portion 25 which is separate from the main body portion of the envelope to permit assembly of the malleable element and the bend-limiting member into the recess 24. This proximal end cone portion 25 is also formed of silicone elastomer material. It will be noted that the envelope 23 terminates in a conical distal end 26. The bend-limiting member 13 is also provided with an elongate element 11a which projects from the distal end thereof into a recess 28 of the envelope 23. Element 11a may preferably be an extension of malleable element 11. The element 11a provides support and some rigidity to the glans area without imparting any undue discomfort to the patient. A rearward extension 11b of malleable element 11 projects into an elongated recess 27 formed in proximal end portion 25 of envelope 23. Extensions 11a and 11b of malleable element 11 distribute bending stresses more evenly over a greater length of the penile prosthesis, and eliminate the stresses which could otherwise concentrate at the opposite ends of bend limiting member 14 if malleable element 11 ended at the same points.

After the prosthesis 10 has been implanted interiorally of the penis, the latter may be oriented to an erect condition when sexual intercourse is desired. When in the erect or phallic position, the malleable element 11 and the bend-limiting member 13 will be in the position as illustrated in FIG. 5. When in the nonerect position, the prosthesis including the malleable element and the bend-limiting member will be bent downwardly. The malleable element 11, when bent, will retain the shape to which it is formed, and will hold the penis in any desired set position.

A different embodiment of the bend-limiting member, designated generally by the reference numeral 30, is shown in FIGS. 6 and 7. The bend-limiting member 30 is in the form of an elongate bellows-like sleeve which may preferably be formed from polypropylene or polyethylene. The corrugated, bellows-like construction of the bend-limiting member defines a plurality of convex portions 31 having concave annual recesses 32 therebetween. The desired flexibility or rigidity of the bend-limiting member can be determined and the bend-limiting member 30 will permit bending of the malleable element 11 about the same radius of bend as the bend-limiting member disclosed in the embodiments of FIGS. 1 through 5. The wall thickness of member 30 and the number of corrugations for a given length primarily determine the bending radius and thus the bending limit. Member 30 may be bent as shown in FIG. 7 until the corrugations on the inner radius are tightly compressed together.

FIG. 9 illustrates a variation of the embodiment of the penile prosthesis shown in FIGS. 1–5. The construction of the outer envelope or casing 23 and bend-limiting member 13 is identical to that shown and described with respect to those figures. The only change is in the arrangement of the strands of filaments 12 comprising the malleable component. The malleable strands 12 are arranged parallel to each other in a generally circular pattern within silicone envelope 23. Rather than being disposed in a tight bundle within bend limiting member 13 as shown in FIG. 8, the strands 12 are arranged around the outside of member 13 generally parallel thereto. The ability of malleable elements 12 to hold the shape to which they are bent permits the penile prosthesis to be selectively bent between erect and nonerect positions.

The penile prosthesis 10 is implanted within the penis through the conventional surgical techniques such as that disclosed in U.S. Pat. No. 3,954,102, entitled "Penile Erection System and Methods of Implanting and Using the Same," filed July 19, 1974, and issued Dec. 1, 1975, and owned by the same assignee as the instant application. The surgical technique disclosed in U.S. Pat. No. 3,954,102 is hereby incorporated by reference.

Generally speaking, the surgical procedure disclosed in U.S. Pat. No. 3,954,102 involves the making of an abdominal incision through the patient's skin to provide access to the pelvic cavity. Erectile tissues within the corpora cavernosa regions of the penis are displaced by an inserted rod in order to create space for the subsequent insertion of a pair of the prosthetic devices 10. It will be appreciated that two such prostheses will be implanted in the penis of each patient. The shape of the prosthesis 10 enables quick insertion into the corpora regions. The end 26 of each prosthesis is first inserted into the corpora regions, until the proximal end portion 25 is positioned within the public symphosis of the patient. It will be appreciated that a variety of diameters and lengths of the prosthesis can be employed where necessary to accommodate differing physical needs.

It is anticipated that various changes can be made in the size, shape and construction of the prosthesis device disclosed herein without departing from the spirit and scope of the invention as defined by the following claims.

What is claimed is:

1. A prosthesis adapted to be implanted in a penis, comprising:
   at least one elongate, malleable element adapted to be selectively conformed to a desired shape,
   an elongate, bend-limiting means positioned in cooperative juxtaposition with said malleable element, along at least a portion of its length said bend-limiting means having a plurality of adjacent elements which engage each other when a predetermined bending radius is reached as the prosthesis is bent, to limit the bending thereof; and,
   an elongate, physiologically inert envelope covering said bend-limiting member and said malleable element.

2. The prosthesis as defined in claim 1 wherein said adjacent elements are hollow and define a hollow bend limiting member, and said malleable element is positioned inside of said bend-limiting member substantially parallel thereto.

3. The prosthesis as defined in claim 2 wherein said malleable element comprises a plurality of elongated, malleable strands.

4. The prosthesis as defined in claim 1 wherein a plurality of elongated, malleable strands are arranged substantially parallel to each other and to said bend-limiting member within said envelope around the outside of said bend-limiting member.

5. The prosthesis as defined in claim 1 wherein said bend-limiting means is comprised of a plurality of similar elongate, hollow elements each having one end portion thereof larger than the other end portion thereof, the smaller end portion of each hollow element projecting into the larger end portion of the next adjacent hollow element, each hollow element of said bend-limiting member being angularly shiftable to a limited degree relative to the adjacent hollow element to permit angular deflection of the bend-limiting means throughout its length and permitting uniform, limited bending of the adjacent malleable element.

6. The prosthesis as defined in claim 5 and a locking element on the smaller end portion of each tubular member cooperatively engaging a locking element on the larger end portion of the next adjacent tubular element to lock said tubular elements together.

7. The prosthesis as defined in claim 6 wherein said locking element on said small end portion of each tubular element comprises a bead and the locking element on the large end portion of each tubular member comprises an annular groove located interiorly of the associated large end portion.

8. The prosthesis as defined in claim 5 wherein said interior of the large end portion of each tubular element tapers axially towards the smaller end portion thereof, and the exterior surface of each small end portion is of substantially uniform diameter.

9. The prosthesis as defined in claim 1 wherein said bend-limiting means comprises an elongate sleeve having a plurality of corrugations defining a bellows construction, whereby the bending of said prosthesis is limited by the compression of the corrugations on the inner radius as bending takes place.

10. The prosthesis as defined in claim 9 wherein said malleable element is positioned inside of said elongate sleeve.

11. The prosthesis as defined in claim 1 wherein said envelope comprises a soft covering of silicone.

* * * * *